(12) United States Patent
Greager et al.

(10) Patent No.: US 7,737,312 B2
(45) Date of Patent: Jun. 15, 2010

(54) PRODUCTION OF LINEAR ALKYL BENZENE

(75) Inventors: Ivan Greager, Sundowner (ZA); Jan Hendrik Scholtz, Parkview (ZA); Johan Pieter de Wet, Vanderbijlpark (ZA); Mieke Ann Desmet, Weltevredenpark (ZA); Wilhelmina Jansen, Vanderbijlpark (ZA); Paul Jacobson, Sasolburg (ZA); Luis Pablo Fidel Dancuart, Vaalpark (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 897 days.

(21) Appl. No.: 10/549,768

(22) PCT Filed: Mar. 10, 2004

(86) PCT No.: PCT/IB2004/000653
§ 371 (c)(1),
(2), (4) Date: Sep. 11, 2006

(87) PCT Pub. No.: WO2004/080926
PCT Pub. Date: Sep. 23, 2004

(65) Prior Publication Data
US 2007/0038007 A1    Feb. 15, 2007

Related U.S. Application Data (60) Provisional application No. 60/453,437, filed on Mar. 10, 2003, provisional application No. 60/453,418, filed on Mar. 10, 2003, provisional application No. 60/462,180, filed on Apr. 11, 2003, provisional application No. 60/496,816, filed on Aug. 21, 2003.

(30) Foreign Application Priority Data

| Mar. 10, 2003 | (ZA) | ................................ 2003/1937 |
| Mar. 10, 2003 | (ZA) | ................................ 2003/1938 |
| Apr. 11, 2003 | (ZA) | ................................ 2003/2868 |
| Aug. 21, 2003 | (ZA) | ................................ 2003/6524 |

(51) Int. Cl.
*C07C 2/68* (2006.01)

(52) U.S. Cl. .................... 585/448; 585/323; 585/446; 585/458; 585/459; 585/464; 585/465; 208/48; 208/49; 208/133; 208/134

(58) Field of Classification Search ............... 585/323, 585/446, 448, 458–459, 464–465; 210/634–643; 208/48–49, 78–79, 134–140
See application file for complete search history.

(56) References Cited

U.S. PATENT DOCUMENTS
3,674,885 A    7/1972   Griesinger et al.
(Continued)

FOREIGN PATENT DOCUMENTS
DE    199 11 910 A1    9/2000
(Continued)

OTHER PUBLICATIONS
Kocal et al., "Production of linear alkylbanzene," *Catalysis*, 2001 (CAS Abstract No. 136:249302).
(Continued)

*Primary Examiner*—Robert J Hill, Jr.
*Assistant Examiner*—Brian McCaig
(74) *Attorney, Agent, or Firm*—Brinks Hofer Gilson & Lione (57) ABSTRACT

This invention relates to a process for producing linear alkyl benzene, the process including the steps of obtaining a hydrocarbon condensate containing olefins, paraffins and oxygenates from a low temperature Fischer-Tropsch reaction; a) fractionating a desired carbon number distribution from the hydrocarbon condensate to form a fractionated hydrocarbon condensate stream; b) extracting oxygenates from the fractionated hydrocarbon condensate stream from step (a) to form a stream containing olefins and paraffins; c) combining the stream containing olefins and paraffins from step (b) with the feed stream from step (g) to form a combined stream; d) alkylating olefins in the combined stream from step (c) with benzene in the presence of a suitable alkylation catalyst in an alkylation reactor; e) recovering linear alkyl benzene from the alkylation reactor; f) recovering unreacted paraffins from the alkylation reactor; g) dehydrogenating the unreacted paraffins in the presence of a suitable dehydrogenation catalyst to form a feed stream containing olefins and paraffins; and h) sending the feed stream containing olefins and paraffins from step (g) to step (c).

27 Claims, 3 Drawing Sheets

U.S. PATENT DOCUMENTS

| | | | |
|---|---|---|---|
| 4,219,686 A | 8/1980 | Petrillo et al. |
| 4,447,664 A | 5/1984 | Murchison et al. |
| 4,513,156 A | 4/1985 | Tabak |
| 4,603,225 A | 7/1986 | Colaianne et al. |
| 4,686,317 A | 8/1987 | Quann et al. |
| 5,196,624 A | 3/1993 | Threlkel et al. |
| 5,196,625 A | 3/1993 | Threlkel et al. |
| 6,111,158 A | 8/2000 | Marinangeli et al. |
| 6,375,830 B1 | 4/2002 | Clark et al. |
| 6,392,109 B1 | 5/2002 | O'Rear et al. |
| 2002/0082182 A1 | 6/2002 | Kott et al. |
| 2002/0115732 A1 | 8/2002 | Moore, Jr. et al. |

FOREIGN PATENT DOCUMENTS

| | | |
|---|---|---|
| EP | 0 807 616 A2 | 11/1997 |
| EP | 1 160 309 A1 | 12/2001 |
| GB | 669313 | 4/1952 |
| GB | 990744 | 4/1965 |
| GB | 2 258 258 A | 2/1993 |
| WO | WO 90/11986 A1 | 10/1990 |
| WO | WO 99/05082 A1 | 2/1999 |
| WO | WO 99/05241 A1 | 2/1999 |
| WO | WO 99/05242 A1 | 2/1999 |
| WO | WO 00/14184 A2 | 3/2000 |
| WO | WO 01/02325 A1 | 1/2001 |
| WO | WO 01/64610 A1 | 9/2001 |
| WO | WO 02/31085 A2 | 4/2002 |
| WO | WO 02/44114 A1 | 6/2002 |

OTHER PUBLICATIONS

Marr et al., "Recent Innovations in linear alkylbenzene process technology," *World Surfactants Congress*, May 29-Jun. 2, 2000, (CAS Abstract No. 136:249396).

Sharma et al., "Synthesis of detergents from Fischer-Tropsch waxes: Part I. Synthesis of heptyl benzene sulphonate," *Research and Industry*, Sep. 20, 1975.

Sharma et al., "Synthesis of detergents from Fischer-Tropsch waxes: Part II. Synthesis of docedyl benzene sulphonate," *Indian J. Technology*, 1977 (CAS Abstract No. 89:56861).

Fig.3

PRODUCTION OF LINEAR ALKYL BENZENE

CROSS REFERENCE TO RELATED APPLICATIONS

The present patent application is the National Stage of International Application No. PCT/IB2004/000653, filed Mar. 10, 2004, which claims the priority of South African Application No. 2003/1937, filed Mar. 10, 2003, claims the benefit under 35 U.S.C. 119(e) of U.S. Provisional Patent Application Ser. No. 60/453,437, filed Mar. 10, 2003, claims the priority of South African Application No. 2003/1938, filed Mar. 10, 2003, claims the benefit of U.S. Provisional Patent Application Ser. No. 60/453,418, filed Mar. 10, 2003, claims the priority of South African Application No. 2003/2868, filed Apr. 11, 2003, claims the benefit of U.S. Provisional Patent Application Ser. No. 60/462,180, filed Apr. 11, 2003, claims the priority of South African Application No. 2003/6524, filed Aug. 21, 2003, and claims the benefit of U.S. Provisional Patent Application Ser. No. 60/496,816, filed Aug. 21, 2003.

BACKGROUND OF THE INVENTION

THIS invention relates to a process for producing linear alkyl benzene.

Alkyl benzene derivatives, such as alkyl benzene sulphonates, are among others, used in detergent and surfactant product applications. Environmental legislation requires that these products are biodegradable. It is well known that, to be bio-degradable, it is important for the alkyl chain to be linear, i.e. with very little or no branching and low, if any, quaternary carbons.

In conventional processes for producing linear alkyl benzenes, a hydrocarbon stream is hydrogenated in order to remove contaminants such as sulphur, nitrogen and oxygen contaminants that may be present. Hydrogenation also converts olefin species in the stream to paraffins. Following the hydrogenation reaction, the resulting paraffin stream is fractionated into various carbon ranges. A carbon range, for example the $C_8$ to $C_{16}$ range, which includes branched paraffins, is passed through a molecular sieve. The branched paraffins are rejected as a raffinate stream, whilst the linear paraffins are passed through a dehydrogenation reactor to form an olefin/paraffin mixture. This mixture is then fed to an alkylation plant and reacted with benzene to form linear alkyl benzene (LAB). The linear alkyl benzene is then sulphonated to form linear alkyl benzene sulphonates (LAS). A problem with this approach is the relatively high cost of paraffinic starting material and the high cost associated with the production of linear paraffins from kerosene feedstocks.

United Kingdom Patent No. 669,313 in the name of California Research Corporation discloses the use of a hydrocarbon condensate from the Fischer-Tropsch process as a feedstock in the production of alkyl benzene. This reference is limited to the use of "high temperature" Fischer-Tropsch processes wherein the Fischer-Tropsch reaction is carried out temperatures of approximately 300° C. and higher, for the production of the hydrocarbon condensate. The high temperature Fischer-Tropsch processes were found to be suitable because the hydrocarbon condensate contains a high concentration of olefins, usually in the region of around 70%. The preferred catalysts in the Fischer-Tropsch process for the production of the hydrocarbon condensate in this reference are iron-containing catalysts. This reference states that Fischer-Tropsch feedstock produced results in poor quality Linear Alkyl Benezene due to odour and wetting problems caused by carbonyl i.e. oxygenate content of the Fischer Tropsch feedstock. The preferred method for addressing this problem is by adsorption of carbonyl compounds from the Fischer Tropsch feedstock using activated carbon and silica gel in a guard bed. This process is only feasible for feeds with low oxygenate concentrations. Also, in the example in this reference the olefin recovery is less than 25%, i.e. the olefin content is not preserved.

U.S. Pat. No. 3,674,885 in the name of Atlantic Richfield Company aims to show that a paraffin/olefin mixture obtained from a Fischer-Tropsch reactor can be alkylated together with chlorinated paraffins by operating the alkylation at elevated temperatures. Fresh Fischer-Tropsch feed is mixed with chlorinated paraffin and charged to the alkylation reactor, the unreacted paraffin is separated and partially activated by chlorination and then mixed with fresh Fischer-Tropsch based feedstock before alkylation. A synthetic mixture of dodecane and dodecene is used in the example to represent Fischer-Tropsch feedstock. This reference does not acknowledge the difficulties faced when attempting to use Fischer-Tropsch feedstock for alkylation and is not considered to be relevant to the present invention.

SUMMARY OF THE INVENTION

According to a first aspect of the invention there is provided a process for producing linear alkyl benzene, the process including the steps of obtaining a hydrocarbon condensate containing olefins, paraffins and oxygenates from a low temperature Fischer-Tropsch reaction;
  a) fractionating a desired carbon number distribution from the hydrocarbon condensate to form a fractionated hydrocarbon condensate stream;
  b) extracting oxygenates from the fractionated hydrocarbon condensate stream from step (a) to form a stream containing olefins and paraffins;
  c) combining the stream containing olefins and paraffins from step (b) with the feed stream from step (g) to form a combined stream;
  d) alkylating olefins in the combined stream from step (c) with benzene in the presence of a suitable alkylation catalyst in an alkylation reactor;
  e) recovering linear alkyl benzene from the alkylation reactor;
  f) recovering unreacted paraffins from the alkylation reactor;
  g) dehydrogenating the unreacted paraffins in the presence of a suitable dehydrogenation catalyst to form a feed stream containing olefins and paraffins; and
  h) sending the feed stream containing olefins and paraffins from step (g) to step (c).

Typically, the low temperature Fischer-Tropsch reaction is carried in a slurry bed reactor at a temperature of 160° C.-280° C., preferably 210° C.-260° C., and in the presence of a cobalt catalyst to provide a hydrocarbon condensate containing 60 to 80% by weight paraffins and 10 to 30% by weight, typically less than 25% by weight, olefins. The olefins so produced having a linearity of greater than 92%, preferably greater than 95%. The paraffins so produced have a linearity greater than 92%.

The oxygenates may be extracted, in step (b), by distillation, dehydration or liquid-liquid extraction, preferably liquid-liquid extraction. A light solvent such as a mixture of methanol and water is preferably used in the liquid-liquid extraction.

In a preferred embodiment of the invention the oxygenate extraction process is a liquid-liquid extraction process that preferably takes place in an extraction column using a mixture of methanol and water as the solvent, wherein an extract from the liquid-liquid extraction is sent to a solvent recovery column from which a tops product comprising methanol, olefins and paraffins is recycled to the extraction column, thereby enhancing the overall recovery of olefins and paraffins. A bottoms product from the solvent recovery column may also be recycled to the extraction column. The solvent preferably has a water content of more than 3% by weight, more preferably a water content of about 5%-15% by weight. A raffinate from the extraction column may be sent to a stripper column from which a hydrocarbon feed stream containing more than 90% by weight olefins and paraffins and typically less than 0.2% by weight, preferably less than 0.02% by weight oxygenates exits as a bottoms product. Preferably the recovery of olefins and paraffins in the hydrocarbon feed stream is in excess of 70%, more preferably in excess of 80%, while the olefin/paraffin ratio is at least substantially preserved.

Typically, the dehydrogenation reaction at step (g) is carried out at a conversion rate of 10%-15%.

Generally, the fractionated hydrocarbon condensate from step (b) will have an olefin concentration of from 10% to 30% by weight, the feed stream from step (g) will have an olefin concentration of 10% to 15% by weight, and the combined stream at step (c) will have an olefin concentration of 12.5% to 22.5% by weight.

The invention also relates to a fractionated hydrocarbon condensate product from a low temperature Fischer-Tropsch reaction in the $C_{10}$ to $C_{13}$ range containing 10 to 30%, typically less than 25%, by weight olefins with a high degree of linearity of greater than 92%, typically greater than 95%, for use in a process for manufacturing linear alkyl benzene.

The invention also relates to a linear alkyl benzene product formed from the alkylation of olefins which are the product a low temperature Fischer-Tropsch reaction, wherein the linear alkyl benzene product has a degree of linearity of greater than 90%, preferably greater than 93%.

According to a second aspect of the invention there is provided a process for producing three hydrocarbon fractions from a hydrocarbon condensate and a wax fraction product stream from a Fischer-Tropsch reaction, the hydrocarbon fractions being:
1) hydrocarbon fraction A, being a hydrocarbon fraction having a boiling point above 25° C. and an end point below 200° C.;
2) hydrocarbon fraction B including at least a mixture of alkanes, olefins and oxygenates having a boiling point in the range 100-300° C.; and
3) hydrocarbon fraction C having a boiling point in the range 120-400° C.;

the method including the steps of:
i) fractionating the hydrocarbon condensate stream, or a derivative thereof, from the Fischer-Tropsch reaction to form at least three fractionated hydrocarbon condensate streams wherein at least one of the three fractionated hydrocarbon condensate streams is hydrocarbon fraction B;
b) hydroconverting at least the wax fraction product stream, or a derivative thereof, from the Fischer-Tropsch reaction;
c) fractionating the hydroconverted wax product from step b) to obtain at least a hydroconverted light hydrocarbon stream and a hydroconverted distillate stream; and
d) selectively blending the products of steps a) and c) to obtain hydrocarbon fractions A and C; and e) transferring the hydrocarbon condensate stream from step (a) that constitutes hydrocarbon fraction B to a process for the production of linear alkyl benzenes.

The process may include the additional step of transferring a waxy unconverted fraction from step b) to a process for the production of high viscosity index base oils by either solvent extraction or catalytic isodewaxing.

Typically, the Fischer-Tropsch reaction is a low temperature Fischer-Tropsch reaction carried out in a slurry bed reactor at a temperature of 160° C.-280° C., preferably 210° C.-260° C., and in the presence of a cobalt catalyst to provide a hydrocarbon condensate containing 60 to 80% by weight paraffins and 10 to 30% by weight, typically less than 25% by weight, olefins.

Typically, the hydrocarbon fraction A has a boiling point above 30° C. and an end point below 175° C., preferably below 160° C.

Typically, the hydrocarbon fraction B has a boiling point in the range is 145-255° C., and preferably the temperature range is 165-240° C.

Typically, the hydrocarbon fraction C has a boiling point in the range 150-380° C., more typically 160-360° C.

The process for the production of linear alkyl benzenes referred to in step e) may comprise alkylation and catalytic dehydrogenation.

According to another aspect of the invention there is provided a process for producing an additional hydrocarbon fraction being hydrocarbon fraction D including medium to high molecular mass alkanes, both linear and isomerised, having a boiling point typically above 380° C., more typically above 400° C.

DESCRIPTION OF PREFERRED EMBODIMENTS

This invention relates to the use of a hydrocarbon condensate stream from a low temperature Fischer-Tropsch reaction in the production of linear alkyl benzene.

In the Fischer-Tropsch process, synthesis gas (carbon monoxide and hydrogen), obtained from gasification of coal or reforming of natural gas is reacted over a Fischer Tropsch catalyst to produce a mixture of hydrocarbons ranging from methane to waxes and smaller amounts of oxygenates.

In a low temperature Fischer-Tropsch reaction, the reaction takes place in a slurry bed reactor or fixed bed reactor, preferably a slurry bed reactor, at a temperature in the range of 160° C.-280° C., preferably 210° C.-260° C., and a pressure in the range of 18-50 bar, preferably between 20-30 bar, in the presence of a catalyst. The catalyst may include iron, cobalt, nickel or ruthenium. However, a cobalt-based catalyst is preferred for the low temperature reaction. Usually, the cobalt catalyst is supported on an alumina support.

During the low temperature Fischer-Tropsch reaction, a lighter hydrocarbon vapour phase is separated from a liquid phase comprising heavier liquid hydrocarbon products. The heavier liquid hydrocarbon product (waxy products) is the major product of the reaction and may, for example, be hydrocracked to produce diesel and naphtha.

The lighter hydrocarbon vapour phase which comprises gaseous hydrocarbon products, unreacted synthesis gas and water is condensed to provide a "condensation product" which comprises an aqueous phase and a hydrocarbon condensation product phase.

The hydrocarbon condensation product includes olefins and paraffins in the $C_4$ to $C_{26}$ range, and oxygenates including alcohols, esters, aldehydes, ketones and acids. Typically, the hydrocarbon condensate product is fractionated into the $C_8$ to $C_{16}$ range, preferably into the $C_{10}$ to a $C_{13}$ range.

In the case of a cobalt catalyst, olefins, which are predominantly alpha olefins, only make up approximately 10 to 30%, by weight, of the fractionated hydrocarbon condensation product. Generally, this product would not be considered useful in an alkylation reaction to form linear alkyl benzene, because of the need to remove oxygenates. Oxygenate removal is required since oxygenates impair the activity of downstream catalysts. This is especially detrimental to solid acid catalysts, such as UOP's Detal catalyst, since it negatively impacts catalyst lifetime, thereby necessitating more frequent catalyst replacement. However, it has been found that the olefins have a very high degree of linearity of greater than 95% and, even though they only make up 10 to 30%, by weight of the hydrocarbon condensate product, it is an excellent feed for the production of linear alkyl benzene and provides an economically advantageous manner for the production of highly linear alkyl benzene. The paraffins in the hydrocarbon condensate product also have a high degree of linearity. These paraffins do not react in the alkylation reaction and are recovered as a high quality paraffin product which is dehydrogenated and recycled to the alkylation reaction. The reactor product from the dehydrogenation process has a relatively low olefin concentration (10%-15% by weight), and the combination of this feed stream with hydrocarbon condensate from the low temperature Fischer-Tropsch reaction increases the olefin concentration in the combined feed provided to the alkylation reaction due to the higher olefin concentration in the hydrocarbon condensate from the low temperature Fischer-Tropsch reaction. This results in a reduction in the recycle flow rate which leads to savings in both capital expenditure and operating costs.

Figure 1:
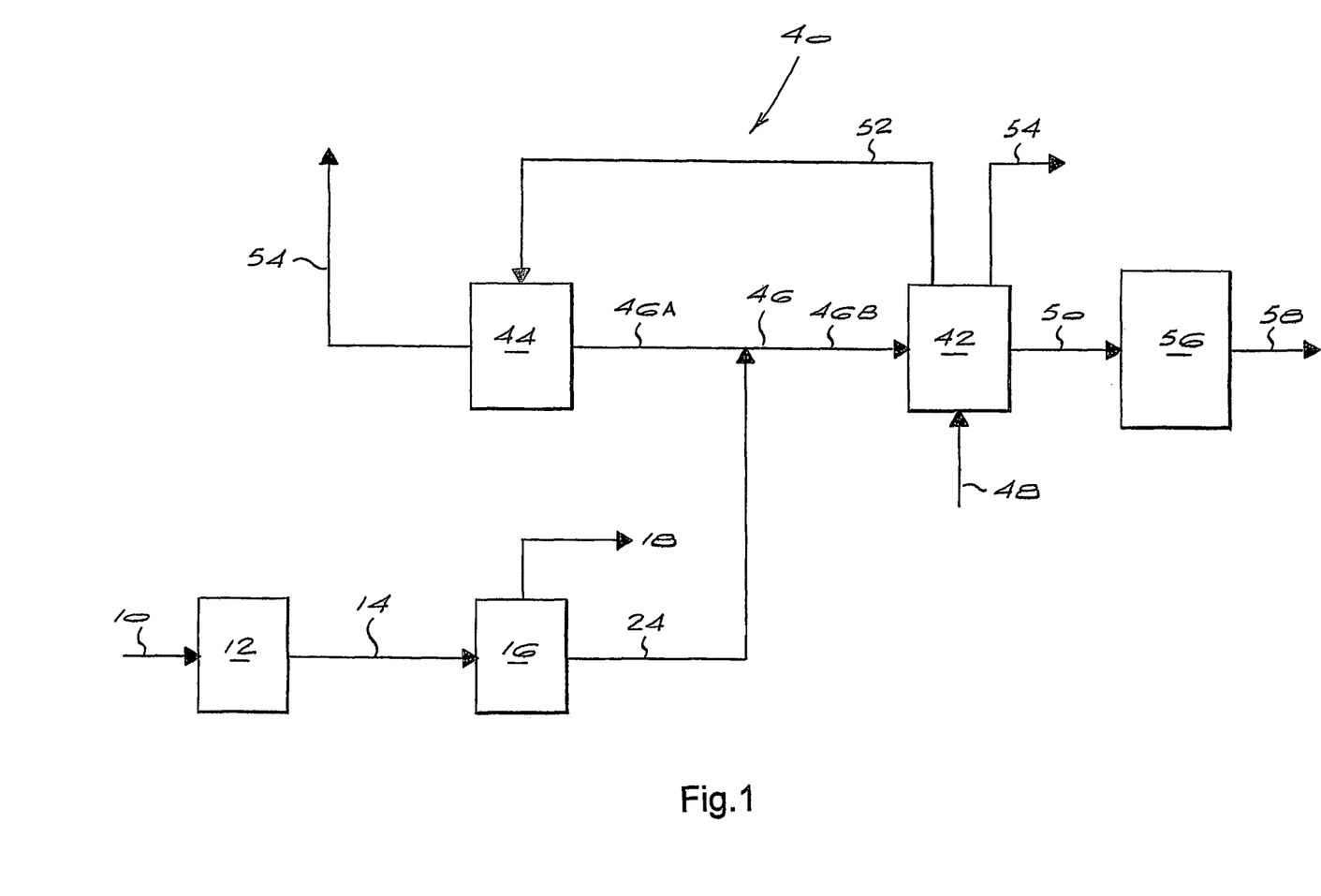
FIG. 1 is a block diagram of a process according to a first aspect of the invention for producing linear alkyl benzene.

Referring to FIG. 1, by way of example of a first aspect of the invention, a hydrocarbon condensation product 10 from a low temperature Fischer-Tropsch reaction using a cobalt catalyst contains 20% by weight olefins, 74% by weight paraffins, and 6% by weight oxygenates. The hydrocarbon condensation product 10 is passed through a fractionation column 12 and a $C_{10}$-$C_{13}$ cut 14 is separated therefrom. The cut 14 contains 22% by weight olefins, 71% by weight paraffins and 7% by weight oxygenates. The cut 14 is then sent to a oxygenate removal unit 16 where the oxygenates 18 are removed to provide a hydrocarbon feed stream 24 containing 23% by weight olefins and 77% by weight paraffins and less than 0.2%, preferably less than 0.015% by weight oxygenates.

As mentioned above, the olefin concentration in the cut 14 is low. It is therefore desirable to use an oxygenate removal step which preserves the olefin concentration. In the prior art, many methods of extracting oxygenates from hydrocarbon streams are suggested. Such removal methods include hydrogenation, azeotropic distillation, extractive distillation, vapour phase dehydration, liquid phase dehydration and liquid-liquid extraction. It has been found that distillation, liquid-liquid extraction and dehydration processes are preferred as they tend to preserve the olefin concentration. Typically the required recovery of olefins and paraffins in stream 24 is larger than 70% of the olefins and paraffins in stream 14, while at least substantially preserving the olefin/paraffin ratio.

Figure 2:
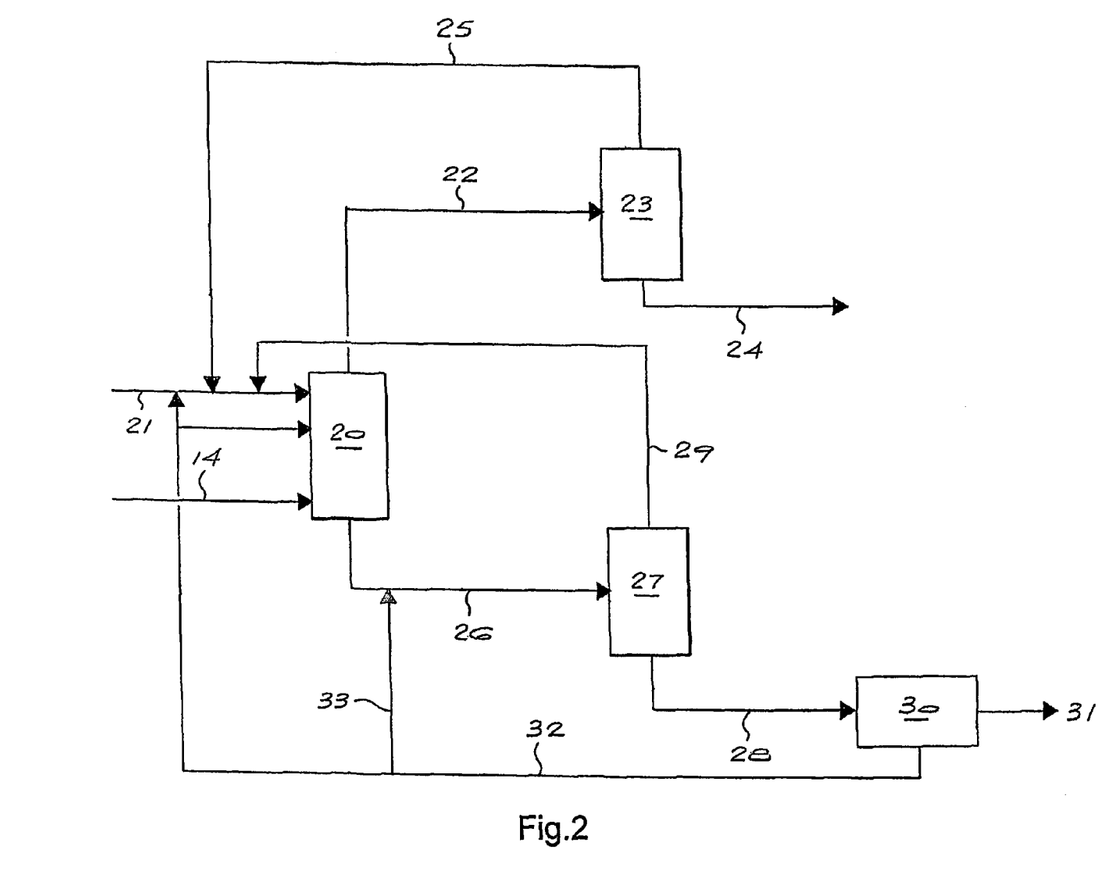
FIG. 2 is a block diagram of a process for extracting oxygenates from a hydrocarbon product, used in the process of FIG. 1.

With reference to FIG. 2, a liquid-liquid extraction process of the invention includes an extraction column 20. The fractionated condensation product of a low temperature Fischer-Tropsch reaction described above 14 is fed into the extraction column 20 at, or near, the bottom thereof and a solvent stream 21 comprising a mixture of methanol and water is fed into the extraction column 20 at or near the top thereof. The solvent stream 21 preferably comprises more than 5% by weight, typically 6% by weight, water. The solvent to feed ratio in the solvent stream is low, typically less than 1.5, usually about 1.25.

Raffinate 22 from the top of the extraction column 20, which includes olefins and paraffins and a small amount of solvent, enters a raffinate stripper column 23 and a hydrocarbon product stream comprising more than 90% by weight olefins and paraffins usually up to 99% by weight olefins and paraffins and less than 0.2% by weight, preferably less than 0.02% by weight oxygenates exits as a bottoms product 24. The bottoms product 24, which shows an overall recovery of over 90% of the olefins and paraffins contains more than 20% by weight α-olefins and more than 70% by weight n-paraffins. Thus, the olefin content of the hydrocarbon product (which is intended for use in the production of linear alkyl benzene) has been preserved. A solvent comprising mainly methanol (more than 90% by weight) and low concentrations of water (less than 5% by weight) and olefins/paraffins (less than 5% by weight) exits as a tops product 25 and is returned to the solvent feed stream 21. If it is desired to recover the bottoms product 24 as a vapour stream, this can be done by taking a bottoms vapour stream from the column 20. The liquid product from the column 20 will then be a very small effluent stream.

An extract 26 is drawn from the bottom of the extraction column 20 and is fed to solvent recovery column 27. A tops product 29 from the solvent recovery column 27 comprises over 90% by weight methanol, and olefins and paraffins. Up to 60% of the olefins and paraffins from the extract 26 are recovered to the tops product 29. The tops product is then recycled to the solvent stream 21. The oxygenate content of the tops product 29 can be as low as 50 ppm, depending on the solvent to feed ratio used in the extraction column 20. A bottoms product 28 from the solvent recovery column 27 comprises mainly water, oxygenates and olefins/paraffins. This bottoms product 28 forms two liquid phases that can be decanted in a decanter 30. The organic phase is an oxygenate, olefin and paraffin stream 31, which leaves the process as a product. The aqueous phase is a stream 32, which is recycled to the extraction column 20. This stream 32 can either enter the extraction column at the top along with the solvent stream 21, or slightly lower down the column 20, to prevent the low amount of oxygenates that will be present in this stream from appearing in the raffinate stream 22.

Normally, a high-boiling solvent is preferred for liquid-liquid extraction because the solvent recovery steps after extraction requires less energy than will be the case for a low-boiling solvent. However, it has been found that a mixture of methanol and water, which is a low-boiling solvent, need not suffer from this drawback, because it can be effective at low solvent to feed ratios (this can be lower than 1 if the required oxygenate extraction is not too severe).

A study of the different azeotropes that exist between components in the feed and water would lead one to expect that it would not be possible to distil water overhead in the solvent recovery column 27 without azeotroping oxygenates overhead as well. Surprisingly, this turns out not to be the case. Methanol, which does not form azeotropes with any of the other species present, prevents the water/oxygenate azeotropes from distilling over at the same temperature as the paraffins and olefins. This appears to be due to an extractive distillation effect. Additionally, it is possible to distil the paraffins and olefins overhead, while recovering the oxygenates as a bottoms product. This has the effect of enhancing the overall paraffin and olefin recovery of the process, because the overheads 29 of the solvent recovery column 27 is recirculated to the extraction column 20, which means that the paraffins and olefins will be forced to leave the process in the product stream 24.

It is therefore possible to have a hydrocarbon stream 24 with a high overall recovery of olefins and paraffins, without the use of a counter solvent in the extraction column. In this mode of operation, all the methanol, and part of the water (10-50%) are also recovered in the overhead stream 29.

When operating a solvent recovery column in the manner described above, it is to be expected that certain species may become trapped in the column. These species will tend to build up and in the process cause unstable operation of the solvent recovery column. Such species would typically be heavier olefins and paraffins or lighter oxygenates in the present case. Operating the solvent recovery column with a small side draw may prevent the build up of such species and thereby result in much improved operability of the system.

It is also possible to run the extraction column 20 and the solvent recovery column 27 at different methanol/water ratios. This may be desirable because a high water content in the extraction column 20 will lead to increased solvent to feed ratios (because of reduced solubility of oxygenates in the solvent), while a certain amount of water is necessary to achieve the extractive distillation effect in combination with methanol to recover all the paraffins and olefins as overhead products in the solvent recovery column 27. The different methanol/water ratios in the two columns (20 and 27) can be achieved by diverting some of the water in stream 32 to stream 26 by means of a stream 33.

After passing the $C_{10}$-$C_{13}$ hydrocarbon feed stream mentioned above through the abovementioned oxygenate extraction process using a mixture of methanol (95% by weight) and water (5% by weight) and a solvent to feed ratio of 1.25, the purified hydrocarbon feed stream 24 contains 22% by weight olefins, 76% by weight paraffins and less than 0.02% by weight oxygenates. Not only does the extraction process extract oxygenates with good recovery of olefins and paraffins, it also preserves the olefin content of the hydrocarbon feed. The recovery of olefins and paraffins is 89.9%, while the ratio of olefins to paraffins is substantially preserved. The purified hydrocarbon feed stream containing olefins is particularly useful in the production of linear alkyl benzene.

The oxygenate removal process may include a final adsorption step to further reduce the oxygenate content to less than 0.015%. The further reduced oxygenate level will depend on the requirements of the chosen alkylation system and may be as low as 0.0001%.

Referring back to FIG. 1, according to the invention the liquid hydrocarbon product 24 from the oxygenate removal process 16 is supplied to an alkylation/dehydrogenation circuit indicated generally by the numeral 40. The alkylation/dehydrogenation circuit 40 includes an alkylation reactor 42 and a dehydrogenation process 44. An alkylation reaction in the alkylation reactor 42 may be carried out by using a Friedel-Crafts type condensation catalyst such as $AlCl_{13}$, $H_2SO_4$, $BF_3$, HF or a solid acid catalyst. In the present case, the UOP DETAL™ solid acid catalyst alkylation technology is used. Typically, the alkylation reaction is carried out at a temperature of greater than 100° C. and a pressure of about 300 Pa (abs), in the presence of UOP's proprietary DETAL™ catalyst (see Smith R. (1991) Linear alkylbenzene by heterogeneous catalysis. PEP Review No. 90-2-4, SRI International).

It is also possible to use reactive distillation (also known as catalytic distillation) to perform the alkylation step, where the catalyst is contained inside a distillation column, and the separation of the unreacted reagents and products occur as soon as the products are formed. In this manner the reactor and product purification functionality are partly combined into a single unit operation.

After alkylation, the unreacted benzene is recovered and recycled to the alkylation reactor 42. The paraffins are recovered and are sent to the dehydrogenation process 44. In the present case, the UOP Pacol™ dehydrogenation technology is used for activation of the paraffins.

Typically, the dehydrogenation reaction is carried out at 400-500° C. and 300 kPa (abs), in the presence of a modified platinum catalyst on an aluminium oxide substrate. Conversion of paraffins to olefins is limited to 10-15% in order to limit further dehydrogenation of mono-olefins to dienes and cyclics. UOP's DEFINE™ and PEP™ processes are used to further remove unwanted by-products from the pacolate, that are formed during dehydrogenation. The DEFINE™ process selectively hydrogenates dienes to the mono-olefins, whilst PEP™ removes cyclic compounds from the pacolate.

With reference to the alkylation/dehydrogenation circuit 40, an olefin-paraffin feed 46 is introduced into the alkylation reactor 42 which is also supplied with benzene 48. The olefins from the olefin paraffin feed 46 react with the benzene 48 in the alkylation reactor 42 to provide linear alkyl benzene 50, unreacted paraffins 52 and unreacted benzene 54. The unreacted benzene 54 is recycled to the alkylation reactor. The unreacted paraffin 52 is recovered and sent to the dehydrogenation process 44 to produce a paraffin olefin mixture 46A which is supplied to the paraffin olefin line 46, and hydrogen 54.

The paraffins 52 leaving the alkylation reactor 42 are of a high quality and comprise substantially 100% paraffin. In this example, the dehydrogenation process 44 operates at a paraffin conversion of 12% and the paraffin olefin mixture 46A leaving the dehydrogenerator 44 has a olefin concentration of 12% and a paraffin concentration of 88%. The hydrocarbon product 28 is introduced mid-way along to the paraffin olefin stream 46. In this example, the hydrocarbon product 24 has an olefin concentration of 23% and a paraffin concentration of 77% and, on mixing with the paraffins and olefins from 46A, form an olefin-paraffin feed stream 46B with an olefin concentration of 13.5% and a paraffin concentration of 86.5%. This increase in olefin concentration in the olefin-paraffin feed stream 46 results in a reduction in the recycle flow rate through the dehydrogenation process 44 and alkylation reactor 42, for a fixed production of linear alkyl benzene. Thus, an increased olefin concentration in the olefin-paraffin feed 46 translates into potential savings in both capital expenditure and operation expenditure. From a capital expenditure perspective, the reduced recycle flow rate allows for a reduction in the size of the dehydrogenation reactor in the dehydrogenation process 44 as well as a reduction in size of the alkylation reactor 42, for a fixed residence time and the reduced paraffin flow rate will allow for a reduction in the size of the paraffin recovery column and ancillary equipment. The operation expenditure savings include a reduced mass flow rate through the dehydrogenation reactor 44 and results in a reduction in the required hydrogen flow rate required for selective hydrogenation of dienes and reduction in the paraffin flow rate will allow for savings in utilities such cooling water, steam (or hot oil) and electricity.

When the alkylation circuit of the process of the present invention is therefore compared with an alkylation circuit of a conventional process for the production of linear alkylbenzene as described in the background to the invention, it can be concluded that a smaller alkylation circuit is required on a per mass of linear alkyl benzene produced, than for the conventional process.

In a final step of the process, the highly linear alkyl benzene 50 with linearity greater than 92% is introduced to a sulphonation reactor 56 and sulphonated using sulphuric acid, oleum or sulphur trioxide. Sulphur trioxide is currently the preferred process. The sulphonation process results in the formation of highly linear alkyl benzene sulphonates 58.

The process of the invention makes use of a feed stream in the form of a condensate product from a low temperature Fischer-Tropsch reaction which would not be expected feasible for producing linear alkyl benzene. The process produces a desirable highly linear alkyl benzene product, while at the same time produces a high quality paraffin product which is dehydrogenated and recycled to the alkylation reaction. The feed stream from the dehydrogenation process has a relatively low olefin concentration (10%-15% by weight), and the combination of this feed stream with hydrocarbon condensate from the low temperature Fischer-Tropsch reaction increases the olefin concentration in the combined feed provided to the alkylation reactor which results in savings in both capital expenditure and operation expenditure.

A second aspect of this invention relates to a process of producing or working-up three pre-determined hydrocarbon fractions from the product streams from a Fischer-Tropsch reaction. These three hydrocarbon fractions include:
1) a hydrocarbon fraction A having a boiling point above the 25° C. and more typically above 30° C., and an end point below 200° C., preferentially below 175° C. and even more preferentially below 160° C.,
2) a hydrocarbon fraction B including a mixture of 60% to 80% by weight alkanes, 15-30% by weight olefins and 5% to 10% by weight oxygenates boiling preferentially in the 100-300° C., and more preferentially in the range 165-240° C. and where the overall linearity of the mixture is greater than 92%, preferentially greater than 95%, and
3) a hydrocarbon fraction C being a hydrocarbon fraction boiling in the range 120-400° C., more typically in the 150-380° C. and preferably in the range 240-360° C.

The invention also extends to producing or working-up a fourth hydrocarbon fraction D including medium to high molecular mass alkanes, both linear and isomerised, boiling typically above 380° C. and preferably above 400° C.

The process as proposed includes the following advantageous features:
1) production of an improved synthetic feedstock for producing linear alkyl benzenes, namely hydrocarbon fraction B; Although fraction B contains oxygenates and has a low olefin content, it can surprisingly be utilized economically/advantageously to produce linear alkyl benzene using the process described in the first aspect of this invention,
2) an improvement in the density and heat content of hydrocarbon fraction C is observed over a process where hydrocarbon fraction B was not removed;
3) production of a high viscosity index (HVI) base oil feedstock—hydrocarbon fraction D. This product can also lead to the recovery of a hydrogenated wax comprising both normal and isomerised alkanes; and
4) production of a high performance feedstock suitable for the production of lower olefins, as described in technical literature (*Performance of the Sasol SPD Naphtha as Steam Cracking Feedstock*, American Chemical Society—Paper 561940, presented at National Meeting, Boston, August 2002).

The production or work up method which forms the subject matter of this aspect of the invention is based on the processing of the two product streams derived from a Fischer-Tropsch reaction, namely a wax fraction product stream and a hydrocarbon condensate:
The wax fraction product stream typically has a true boiling point (TBP) in the range of about 70° C. to 700° C., more typically in the range 80° C. to 650° C.
The hydrocarbon condensate typically has a true boiling point (TBP) in the range −70° C. to 350° C., more typically −10° C. to 340° C., usually −70° C. to 350° C.

A typical composition of the wax fraction product stream and the hydrocarbon condensate is set out in Table 1.

TABLE 1

| Distillation Range | (vol % distilled) | |
|---|---|---|
| | Hydrocarbon Condensate | Wax Fraction Product Stream |
| C5-160° C. | 44 | 3 |
| 160-270° C. | 43 | 4 |
| 270-370° C. | 13 | 25 |
| 370-500° C. | NR | 40 |
| >500° C. | NR | 28 |
| Total | 100 | 100 |

The hydrocarbon condensate includes olefins and paraffins in the $C_4$ to $C_{26}$ range, and oxygenates including alcohols, esters, aldehydes, ketones, acetals and acids.

Figure 3:
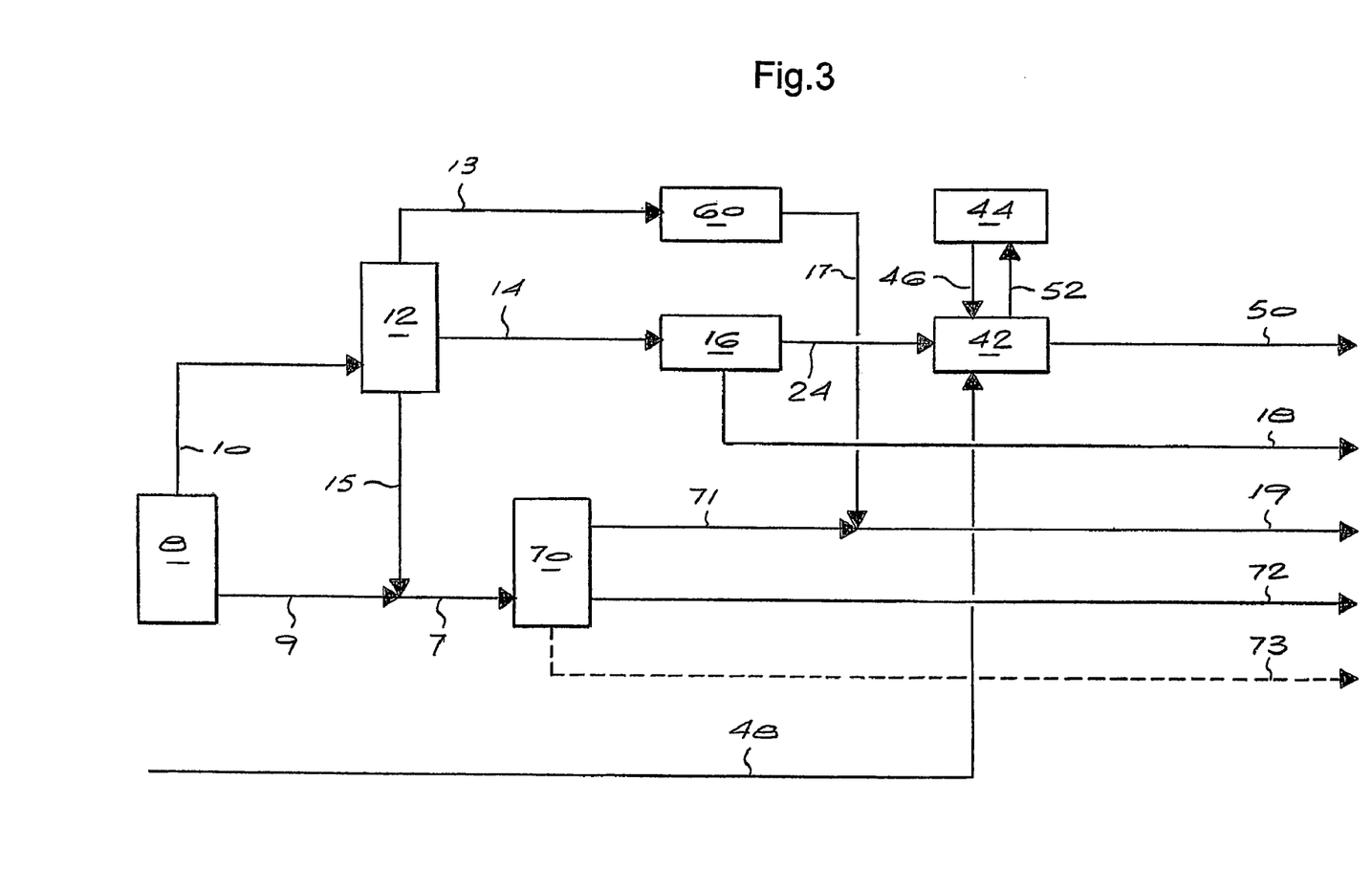
FIG. 3 is a block diagram of an integrated process according to a second aspect of the invention.

An embodiment of this second aspect of the invention is exemplified with reference to FIG. 3. In this embodiment two liquid hydrocarbon products are separated from the conversion of synthesis gas (syngas) by the Fischer-Tropsch reaction in a Fischer-Tropsch reaction unit 8.

The hydrocarbon condensate is collected as stream 10 and transferred to an atmospheric distillation unit (ADU) 12 where it is separated into three streams. The lighter stream 13 is transferred to a hydrotreater 60 for complete saturation and removal of heteroatoms. (This step is optional to the process.) The resulting product is collected as stream 17. A middle stream 14 is collected as a second product and transferred to a linear alkyl benzene processing operation. A heavier hydrocarbon fraction is collected as stream 15 and transferred to a hydroconversion unit 70.

The wax fraction product stream 9 from the Fischer-Tropsch reaction unit 8, is blended with stream 15 from the ADU 12 before being sent as stream 7 to the hydroconversion unit 70. Here at least three products are produced as well as a mixture of light hydrocarbons (not shown in the figure) as a gaseous stream. A light hydrocarbon product stream 71 and a heavier hydrocarbon product stream 72 is sent to storage. There is a fourth stream that is produced—also not shown in the figure—that includes all heavy unconverted hydrocarbon species. This is usually recycled to extinction within the hydroconversion unit 70. As an alternative to the process, a heavy hydroconverted stream can be recovered as stream 73 and made available for the preparation of high visibility index (HVI) base oils by either solvent extraction or catalytic dewaxing. These two processing options are well known in the art and are not described in detail here. Should solvent extraction be used, it is possible to obtain as a by-product a highly paraffinic hydrogenated wax.

Stream 14, the middle stream from the ADU 12, which contains synthetic olefinic feedstock is sent to linear alkyl benzene processing starting with unit 16. Unit 160 is an oxygenates removal unit operation as illustrated in FIG. 2. Two streams are obtained from the oxygenate removal unit 16: an oxygenates rich stream 18 sent to storage, and a stream 24 comprising mostly paraffins and olefins. This stream is the stream "B" having a boiling point in the range 100-300° C. The stream 24 is sent to the alkylation unit 42 where it is alkylated with benzene 48 transferred from storage. The products from the alkylation unit 42 are separated into two streams: the linear alkyl benzene product 50 and an unconverted stream 52. The latter stream 52, comprising paraffins, is sent to the dehydrogenation unit 44 to undergo catalytic dehydrogenation. Once processed, this is returned via stream 46 to the alkylation unit 42.

The two light liquid hydrocarbon streams, hydrotreated product 17 and hydroconverted product 71 are blended to form a highly paraffinic single stream 19.

Process conditions for hydrotreating and hydroconversion of streams from a Fischer-Tropsch reaction unit can be varied to achieve a wide range of product compositions. The process conditions are usually laboriously chosen after extensive experimentation to optimise yields, process performance and catalyst life. Table 2 gives a list of one such set of typical conditions.

TABLE 2

| Set of Conditions | Process Conditions for Hydroprocessing of the Fischer-Tropsch Streams | | | |
|---|---|---|---|---|
| | Hydrotreating Range | | Hydroconversion Range | |
| | Broad | Preferred | Broad | Preferred |
| Temperature, °C. | 150-450 | 250-350 | 150-450 | 340-400 |
| Pressure, bar-g | 10-200 | 30-80 | 10-200 | 30-80 |
| $H_2$ rate, $m^3n/m^3$ feed | 100-2000 | 800-1600 | 100-2000 | 800-1600 |
| Conversion (note 1) | NA | NA | 30-80 | 50-70 |

Note 1
Expressed as material boiling above 370° C. that disappears during the process (mass %)

The extraction step of the invention will now be described in more detail with reference to the following non-limiting example.

EXAMPLE

This example shows a process according to the invention. The extraction column 20 was run at a solvent to feed ratio of 1.25 and a temperature of 50° C. The overall olefin/paraffin recovery in the stream 24 was 89.9%. The olefin/paraffin ratio in the feed was 1:3.7 and 1.36 post oxygenate extraction. The olefin/paraffin ratio was therefore substantially preserved.

Extraction column 20

| | Stream | | | | | | | |
|---|---|---|---|---|---|---|---|---|
| | 14 | | 21 | | 22 | | 26 | |
| | Comp (wt %) | Flow (kg/hr) | Comp (wt %) | Flow (kg/hr) | Comp (wt %) | Flow (kg/hr) | Comp (wt %) | Flow (kg/hr) |
| Total | 100 | 3000 | 100 | 3750 | 100 | 2530 | 100 | 4220 |
| Total C10-C13 P/O | 92.7 | 2779.7 | 2.16 | 81.0 | 99.1 | 2507.9 | 6.20 | 261.7 |
| Total Oxygenates | 7.3 | 217.7 | 0.000 | 0.000 | 0.0144 | 0.365 | 5.78 | 243.7 |
| Lights and Heavies | 0.057 | 1.7 | 0.004 | 0.144 | 0.0104 | 0.263 | 0.00480 | 0.202 |
| Water | 0.031 | 0.934 | 6.01 | 225.6 | 0.0073 | 0.184 | 5.74 | 242.4 |
| Methanol | 0.000 | 0.000 | 91.7 | 3443.3 | 0.842 | 21.31 | 82.3 | 3472.0 |

Raffinate Stripper column 23

| | Stream | | | | | |
|---|---|---|---|---|---|---|
| | 22 | | 25 | | 24 | |
| | Comp (wt %) | Flow (kg/hr) | Comp (wt %) | Flow (kg/hr) | Comp (wt %) | Flow (kg/hr) |
| Total | 100 | 2530 | 100 | 30 | 100 | 2500 |
| Total C10-C13 P/O | 99.1 | 2507.9 | 2.63 | 0.793 | 99.97 | 2499.4 |
| Total Oxygenates | 0.0144 | 0.365 | 0.00163 | 0.000491 | 0.0145 | 0.363 |
| Lights and Heavies | 0.0104 | 0.263 | 0.0887 | 0.0267 | 0.00808 | 0.202 |
| Water | 0.0073 | 0.184 | 1.52 | 0.456 | 0.00115 | 0.0288 |
| Methanol | 0.842 | 21.31 | 95.4 | 28.7 | 0.000 | 0.000 |

| | Solvent Recovery column 27 | | | | | |
|---|---|---|---|---|---|---|
| | Stream | | | | | |
| | 26 | | 29 | | 28 | |
| | Comp (wt %) | Flow (kg/hr) | Comp (wt %) | Flow (kg/hr) | Comp (wt %) | Flow (kg/hr) |
| Total | 100 | 4220 | 100 | 3584 | 100 | 636 |
| Total C10-C13 P/O | 6.20 | 261.7 | 2.37 | 85.1 | 27.6 | 175.8 |
| Total Oxygenates | 5.78 | 243.7 | 0.00140 | 0.0503 | 42.0 | 267.0 |
| Lights and Heavies | 0.00480 | 0.202 | 0.00747 | 0.268 | 0.00279 | 0.0177 |
| Water | 5.74 | 242.4 | 1.30 | 46.8 | 29.3 | 186.6 |
| Methanol | 82.3 | 3472.0 | 96.2 | 3451.9 | 1.04 | 6.63 |

The invention claimed is:

1. A process for producing linear alkyl benzene, the process including the steps of obtaining a hydrocarbon condensate containing olefins, paraffins and oxygenates from a low temperature Fischer-Tropsch reaction;

a) fractionating a desired carbon number distribution from the hydrocarbon condensate to form a fractionated hydrocarbon condensate stream which is the product of a Fischer-Tropsch reaction;

b) extracting oxygenates from the fractionated hydrocarbon condensate stream from step (a) to form a stream containing olefins and paraffins which is the product of a Fischer-Tropsch reaction;

c) combining the stream containing olefins and paraffins from step (b), which is the product of a Fischer-Tropsch reaction, with the feed stream from step (g) to form a combined stream;

d) alkylating olefins in the combined stream from step (c) with benzene in the presence of a suitable alkylation catalyst in an alkylation reactor;

e) recovering linear alkyl benzene from the alkylation reactor;

f) recovering unreacted paraffins from the alkylation reactor;

g) dehydrogenating the unreacted paraffins in the presence of a suitable dehydrogenation catalyst to form a feed stream containing olefins and paraffins; and h) sending the feed stream containing olefins and paraffins from step (g) to step (c).

2. A process according to claim 1, wherein, in the extraction step b), the ratio of olefins to paraffins is substantially preserved.

3. A process according to claim 1, wherein the low temperature Fischer-Tropsch reaction is carried in a slurry bed reactor at a temperature of 160° C.-280° C. and in the presence of a cobalt catalyst to provide a hydrocarbon condensate containing 60 to 80% by weight paraffins and 10 to 30% by weight olefins.

4. The process according to claim 3, wherein the Fischer-Tropsch reaction is carried out at a temperature of 210° C.-260° C.

5. The process according to claim 3, wherein the hydrocarbon condensate contains 10 to less than 25% by weight olefins.

6. The process according to claim 3, wherein the olefins in the hydrocarbon condensate have a linearity of greater than 92%.

7. The process according to claim 6, wherein the olefins in the hydrocarbon condensate have a linearity of greater than 95%.

8. The process according to claim 3, wherein the paraffins in the hydrocarbon condensate have a linearity greater than 92%.

9. The process according to claim 1, wherein the Fischer-Tropsch reaction is carried out in the presence of a cobalt catalyst.

10. The process according to claim 1, wherein the hydrocarbon condensate is fractionated, in step a), into the $C_8$ to $C_{16}$ range.

11. The process according to claim 10, wherein the hydrocarbon condensate product is fractionated, in step a), into the $C_{10}$ to $C_{13}$ range.

12. The process according to claim 11, wherein the fractionated hydrocarbon product contains 10 to 30% by weight olefins with a degree of linearity greater than 92%.

13. The process according to claim 1, wherein the oxygenates are extracted, in step (b), by distillation, dehydration or liquid-liquid extraction.

14. The process according to claim 13, wherein the oxygenates are extracted by liquid-liquid extraction.

15. The process according to claim 14, wherein a light solvent is used in the liquid-liquid extraction.

16. The process according to claim 15, wherein the light solvent is a mixture of methanol and water.

17. The process according to claim 16, wherein the oxygenate extraction process is a liquid-liquid extraction process that takes place in an extraction column using a mixture of methanol and water as the solvent, wherein an extract from the liquid-liquid extraction is sent to a solvent recovery column from which a tops product comprising methanol, olefins and paraffins is recycled to the extraction column, thereby enhancing the overall recovery of olefins and paraffins.

18. The process according to claim 17, wherein a bottoms product from the solvent recovery column is recycled to the extraction column.

19. The process according to claim 17, wherein a raffinate from the extraction column is sent to a stripper column from which a hydrocarbon feed stream containing more than 90% by weight olefins and paraffins and less than 0.2% by weight oxygenates exits as a bottoms product.

20. The process according to claim 19, wherein the hydrocarbon feed stream contains less than 0.02% by weight oxygenates.

21. The process according to claim 16, wherein the solvent has a water content of more than 3% by weight.

22. The process according to claim 21, wherein the solvent has a water content of from 5%-15% by weight.

23. The process according to claim 1, wherein the recovery of olefins and paraffins in the hydrocarbon feed stream over the extraction step b) is in excess of 70%.

24. The process according to claim 23, wherein the recovery of olefins and paraffins in the hydrocarbon feed stream is in excess of 80%.

25. The process according to claim 1, wherein the olefin/paraffin ratio of the fractionated hydrocarbon condensate stream a) is substantially preserved over the extraction step b).

26. The process according to claim 1, wherein the dehydrogenation reaction at step (g) is carried out at a conversion rate of 10%-15%.

27. The process according claim 26, wherein the fractionated hydrocarbon condensate from step (b) has an olefin concentration of from 10% to 30% by weight, the feed stream from step (g) has an olefin concentration of 10% to 15% by weight, and the combined stream at step (c) has an olefin concentration of 12.5% to 22.5% by weight.

* * * * *